United States Patent [19]

Fujiyasu et al.

[11] Patent Number: 4,610,802

[45] Date of Patent: Sep. 9, 1986

[54] METHOD OF ACTIVATING THIOUREA DIOXIDE

[75] Inventors: Koichiro Fujiyasu; Shigeki Yoneyama; Haruhiko Ito, all of Fuji, Japan

[73] Assignee: Tokai Denka Kogyo Kabushiki Kaisha, Tokyo, Japan

[21] Appl. No.: 660,385

[22] Filed: Oct. 12, 1984

[30] Foreign Application Priority Data

Dec. 29, 1983 [JP] Japan .................. 58-246246

[51] Int. Cl.⁴ ............................................. C09K 3/00
[52] U.S. Cl. .................. 252/188.2; 252/105; 252/188.31
[58] Field of Search .............. 252/105, 188.2, 188.25, 252/188.26, 188.27, 188.31; 430/407, 410

[56] References Cited

U.S. PATENT DOCUMENTS

| | | | |
|---|---|---|---|
| 2,339,309 | 1/1944 | Weber et al. ............. | 430/407 X |
| 2,847,351 | 8/1958 | Brown et al. ............. | 252/188.2 X |
| 2,860,944 | 11/1958 | Young ...................... | 8/110 |
| 3,049,445 | 8/1962 | Lundgren et al. ........ | 427/354 |
| 3,060,142 | 10/1962 | Furness .................... | 524/787 |
| 3,077,370 | 2/1963 | Kilby et al. ............... | 8/585 |
| 3,104,150 | 9/1963 | Dadoly et al. ............ | 8/530 |
| 3,244,473 | 4/1966 | Wegmann et al. ........ | 252/105 |
| 3,344,128 | 9/1967 | Uraneck ................... | 526/94 |
| 3,384,534 | 5/1968 | Kindron et al. .......... | 162/71 |
| 4,240,791 | 12/1980 | Sato et al. ................ | 252/188.2 X |
| 4,244,690 | 1/1981 | Sato et al. ................ | 252/188.2 X |

Primary Examiner—Edward A. Miller
Assistant Examiner—Matthew A. Thexton
Attorney, Agent, or Firm—Scully, Scott, Murphy & Presser

[57] ABSTRACT

Activating thiourea dioxide is characterized by incorporating in the thiourea dioxide a substance which dissolves in water or an acidic aqueous solution and produces hydrogen.

4 Claims, 4 Drawing Figures

METHOD OF ACTIVATING THIOUREA DIOXIDE

BACKGROUND OF THE INVENTION

The present invention relates to a method of activating thiourea dioxide.

Thiourea dioxide is also called formamidine-sulfinic acid or aminoiminomethanesulfinic acid and is often abbreviated as TDO or TUD.

Thiourea dioxide is a powdered stable compound, which dissolves in water and decomposes gradually to exhibit a reducing action. But, this reaction is slow, and particularly in an acidic to weakly alkaline region thiourea dioxide is stable and its reducing action is weak.

Usually, thiourea dioxide dissolves in water and produces sulfoxylic acid through formamidine-sulfinic acid. This reaction is promoted by the application of heat or in the presence of an alkali, and a strong reducing action is thereby exhibited.

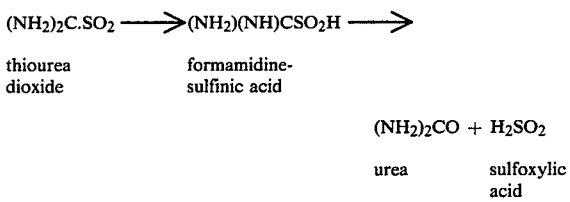

The only method for promoting the reaction in an acidic to weakly alkaline region is to raise the temperature. In the case where raising the temperature is restricted for some reason, it has heretofore been unavoidable for thiourea dioxide to be used in an uneconomical state in which it cannot fully exhibit its effect. Further, also in the utilization of thiourea dioxide in an alkaline region, although thiourea dioxide produces a very stable sulfoxylic acid, its sulfoxylic acid producing speed is slow as compared with sodium hydrosulfite (hereinafter referred to simply as "hydrosulfite") which is a reducing agent in wide use, so when it is desired to utilize a quick effect in a short time, it has heretofore been impossible for thiourea dioxide to fully exhibit its reducing power latent therein.

Thus, heretofore there have been many cases where thiourea dioxide cannot fully exhibit its reducing power. But, there are various uses thereof. For example, in the textile industry, it has been utilized as a reducing agent for vat dye (see U.S. Pat. Nos. 3,104,150 and 3,077,370 and Japanese Patent Publication Nos. 37630/1980, 37631/1980, 37632/1980, 37633/1980, 37634/1980, 37635/1980 and 5904/1982), further utilized for discharging of printed cloth (see German Pat. No. 941,363), bleaching of protein fibers (see Japanese Patent Publication No. 15648/1968), shrink proofing (U.S. Pat. No. 3,049,445) and reduction clearing of cloth dyed with disperse dye (see Japanese Patent Publication No. 27277/1977); in the paper pulp industry it has been utilized for bleaching of wood pulp (see U.S. Pat. Nos. 2,860,944 and 3,384,534 and British Pat. No. 1,079,135); in the photographic industry, as an auxiliary agent of developer (see Belgian Pat. No. 547,323 and German Pat. No. 942,777); in the cosmetic industry, as an auxiliary agent for hair waving (see German Pat. No. 1,083,986). Such uses as a reducing agent for high polymer polymerization (see U.S. Pat. Nos. 3,344,128 and 3,060,142), a detergent composition (see Japanese Patent Publication No. 3811/1974) and a precipitant for heavy metals in water (see Japanese Patent Publication No. 12188/1976) are also known.

SUMMARY OF THE INVENTION

It is the object of the present invention to provide an effective activating method for thiourea dioxide.

The above object of the present invention is attained by incorporating in thiourea dioxide a substance which dissolves in water or an acidic aqueous solution and produces hydrogen.

According to the method of the present invention, thiourea dioxide can be activated to a remarkable extent in an acidic to weakly alkaline region in which region no other effective means than heating has heretofore been available, and even in an alkaline region there can be attained a rapid formation of sulfoxylic acid and a further promotion of activation.

DETAILED DESCRIPTION OF THE PREFERRED EMBODIMENTS

As the substance (hereinafter referred to as the "activating agent") used in the method of the present invention which substance dissolves in water or an acidic aqueous solution and produces hydrogen, there may be used any known hydrogen-producing reducing substance, examples of which include such metals as K, Na, Mg, Al, Zn and Sn in the order of ionization tendency. Inorganic compounds such as sodium, lithium, potassium and aluminum salts of borohydride as well as lithium aluminum hydride are also preferred. The activating agent just exemplified may be used alone or in combination of two or more.

By adding the activating agent into an aqueous solution containing thiourea dioxide, the reduction potential is raised, which value is higher than those exhibited by thiourea dioxide and the activating agent each independently. This fact means that thiourea dioxide is activated.

The amount of the activating agent used is not less than 0.01, preferably not less than 0.1, in terms of a reduction equivalent of thiourea dioxide to that of hydrogen produced ratio (H/TDO). The upper limit of the activating agent used is not specially limited, but usually it is not more than 1.0 as such ratio. Optimum amount of the activating agent used may be determined according to the use and the purpose of use of thiourea dioxide, economy, etc.

Thiourea dioxide is used as an aqueous solution according to purposes of use. The activating agent may be added into the aqueous solution, or alternatively it may be incorporated in a solid composition containing thiourea dioxide before use.

The concentration of the aqueous solution of thiourea dioxide is preferably not lower than 0.05 g/l. Lower concentrations would result in a poor maintainability of the state of reduction and a too rapid decomposition of thiourea dioxide. Its upper limit is not specially limited, but usually it is not higher than 5 g/l.

The effect of the activating agent is remarkable particularly when it is used at an ordinary temperature of about 20° to 22° C., although its effect does not disappear even at temperatures below 20° C. At temperatures not lower than 20° C., the reduction potential becomes higher. Usually, the activating agent is used as a temperature in the range of about 10° to 50° C.

By selecting the kind of the activating agent to be used, there can be obtained a remarkable effect of activation over a wide pH range. For example, in an alkaline to strongly alkaline region in which there are many examples of use of thiourea dioxide, alkali metal salts of borohydride exhibit an especially outstanding activation effect. More particularly, under fiber dyeing conditions, e.g. thiourea dioxide 1 g/l, caustic soda 4 g/l and temperature 50° C., about three minutes are required for reaching −900 mV (platinum electrode/reference electrode) or higher which potential is peculiar to thiourea dioxide. On the other hand, if sodium borohydride is added in an amount of 0.05 g/l (SBH/TDO=0.29), −900 mV is reached in about 40 seconds. Further, although in the absence of the activating agent there temporarily occurs a stagnation of potential in a time period between 30 and 60 seconds, this phenomenon disappears in the presence of the activating agent.

The pH of the aqueous solution containing thiourea dioxide may be adjusted by any suitable method. For example, it may be adjusted by the addition of mineral acids such as hydrochloric, sulfuric and phosphoric acids, organic acids such as formic, acetic and citric acids, or salts thereof, or caustic soda, soda ash, sodium silicate, ammonia, sodium pyrophosphate or sodium tripolyphosphate.

Further, in order to stabilize the sulfoxylic acid produced from thiourea dioxide, there may be employed a chelating agent, examples of which include aminopolycarboxylates such as sodium nitrilotriacetate, sodium ethylenediaminetetraacetate and sodium diethylenetriaminepentaacetate.

Reducing agents not releasing hydrogen ion, e.g. hydrosulfite and Rongalit (sodium sulfoxylate formaldehyde or hydroxy methane sulfinic acid), have also been studied, but these reducing agents when used in combination with thiourea dioxide were found to exhibit no activating action for thiourea dioxide, merely exhibiting reduction potentials peculiar thereto.

The following Examples are given to further illustrate the present invention.

The measurement of potential was performed using a platinum electrode and a saturated silver/silver chloride electrode as a reference electrode by means of a potentiometer Model HM-5 (a product of Toa Electronics Ltd.).

EXAMPLE 1

Various activating agents were added to solutions containing 0.5 g/l of thiourea dioxide and having pH values in the range of 5.5 to 6.5 adjusted with sodium phosphate and citric acid, and redox potentials were measured at 20°–22° C. and compared.

| Thiourea Dioxide | Activating Agent | Amount g/l | pH | Potential mV |
|---|---|---|---|---|
| 0 g/l | Sodium hydrosulfite | 0.2 | 6.0 | −495 |
| 0.5 | Sodium hydrosulfite | 0.15 | 6.0 | −490 |
| 0 | Rongalit C | 0.2 | 5.8 | +55 |
| 0.5 | " | 0.18 | 5.9 | +60 |
| 0 | Sodium borohydride | 0.05 | 5.6 | −305 |
| 0.5 | Sodium borohydride | 0.05 | 5.8 | −690 |
| 0 | Lithium borohydride | 0.05 | 5.8 | −295 |
| 0.5 | Lithium borohydride | 0.05 | 5.8 | −695 |
| 0 | Lithium aluminum hydride | 0.05 | 6.2 | −240 |
| 0.5 | Lithium aluminum hydride | 0.05 | 6.1 | −580 |
| 0.5 | — | — | 6.0 | +120 |

EXAMPLE 2

Metal zinc (Zn) was added to solutions containing 1.0 g/l of thiourea dioxide (TDO) and having a pH value of 1.5 adjusted with HCl, and changes of redox potential were measured at 21° C.

| (TDO) Thiourea Dioxide (g/l) | (Zn) Metal Zinc (g/l) | Zn/TDO Reduction Equivalent Ratio | Redox Potential mV |
|---|---|---|---|
| 1.0 | — | — | −247 |
| — | 0.34 | — | −200 |
| 1.0 | 0.34 | 0.29 | −440 |
| — | 0.68 | — | −220 |
| 1.0 | 0.68 | 0.56 | −450 |

EXAMPLE 3

0.24 g/l of metal sodium was added to aqueous solutions containing 1.0 g/l of thiourea dioxide, and redox potentials were measured at 20°–22° C. The mark * shown below indicates that acetic acid and sodium phosphate were used for the adjustment of pH.

| (TDO) Thiourea Dioxide (g/l) | (Na) Metal Sodium (g/l) | Reduction Equivalent Ratio | pH | Redox Potential mV |
|---|---|---|---|---|
| *1.0 | — | — | 5.6 | +130 |
| *— | 0.24 | — | 6.0 | +70 |
| *1.0 | 0.24 | 0.29 | 6.0 | −130 |
| 1.0 | 0.24 | 0.29 | 10.1 | −650 |

EXAMPLE 4

1 g/l of thiourea dioxide (TDO) and 0.05 g/l of sodium borohydride (SBH) were used each indepenedently and also as a mixture, and changes of reduction potential were measured at 20°–22° C. in a pH range of 2 to 13.

| Thiourea Dioxide (TDO) Sodium Borohydride (SBH) | Comparative Example 1 1 (g/l) 0 | Comparative Example 2 0 (g/l) 0.05 | Example 4 1 (g/l) 0.05 |
|---|---|---|---|
| pH 2.3 | +210 (mV) | −270 (mV) | −250 (mV) |
| 3.7 | +180 | −300 | −310 |
| 4.4 | +150 | −320 | −360 |
| 5.1 | +110 | −340 | −450 |
| 6.1 | +60 | −360 | −640 |
| 7.3 | +5 | −370 | −640 |
| 8.5 | −130 | −380 | −650 |
| 9.3 | −210 | −380 | −670 |
| 10.0 | −230 | −390 | −690 |
| 11.1 | −680 | −390 | −710 |
| 12.0 | −720 | — | −730 |
| 13.1 | −750 | — | −755 |

At an SBH/TDO reduction equivalent ratio of 0.29 there was recognized a remarkable improvement of reduction potential, and it is seen that particularly in the pH range of 6 to 11 potentials close to that at pH 11 in the absence of SBH are exhibited and that even at the pH values below 6 a fairly high potential is exhibited.

EXAMPLE 5

Using 1 g/l of thiourea dioxide (TDO) and 0.01 to 0.1 g/l of sodium borohydride (SBH) (SBH/TDO reduction equivalent ratio: 0.06-0.58), reduction potentials were measured at 20°-22° C. in the pH range of 6 to 8.

| SBH (g/l) | SBH/TDO Reduction Equivalent Ratio | Reduction Potential mV |
|---|---|---|
| 0 | — | +10 |
| 0.01 | 0.06 | −480 |
| 0.02 | 0.12 | −705 |
| 0.05 | 0.29 | −710 |
| 0.07 | 0.40 | −715 |
| 0.1 | 0.58 | −730 |

EXAMPLE 6

Using 0.1 to 1 g/l of thiourea dioxide (TDO) and sodium borohydride (SBH) at SBH/TDO reduction equivalent ratios of 0.14, 0.29 and 0.57, changes of potential were measured at 20°-22° C. in the pH range of 6 to 8.

| | SBH/TDO Reduction Equivalent Ratio | | | |
|---|---|---|---|---|
| TDO | 0 | 0.14 | 0.29 | 0.57 |
| 0.05 | +50 | +30 | −400 | −695 |
| 0.1 | +90 | −20 | −445 | −710 |
| 0.25 | +80 | −270 | −560 | −740 |
| 0.5 | +110 | −580 | −670 | −760 |
| 0.75 | +120 | −660 | −720 | −770 |
| 1.0 | +150 | −705 | −715 | −740 |

EXAMPLE 7

0.03 g/l of lithium borohydride (LiBH) was added to 0.75 g/l of thiourea dioxide (TDO), and reduction potentials were measured at pH 5 and at varied temperatures of 20° to 80° C.

| | TDO | TDO, LiBH |
|---|---|---|
| 20° C. | +120 | −380 |
| 40° C. | +80 | −510 |
| 60° C. | −10 | −560 |
| 80° C. | −150 | −620 |

EXAMPLES 8-9

Solutions each containing 1 g/l of thiourea dioxide (TDO) and 4 g/l of caustic soda were heated to 50° C. and 75° C., respectively, and reduction potentials were measured at every 20 seconds, results of which were compared with those obtained by using solutions each containing 0.05 g/l of sodium borohydride (SBH) in addition to 1 g/l of thiourea dioxide and 4 g/l of caustic soda.

At a SBH/TDO (reduction equivalent ratio) of 0.29, a very rapid increase of reduction potential was recognized and high reduction potentials were obtained in a short time at both 50° C. and 75° C.

| Sodium Boro-hydride | Comparative Example 3 50° C. | Example 8 | Comparative Example 4 75° C. | Example 9 |
|---|---|---|---|---|
| | 0 | 0.05 g/l | 0 | 0.05 g/l |
| 0 (second) | −210 mV | −190 mV | −200 mV | −200 mV |
| 5 | — | — | −700 | −920 |
| 20 | −620 | −720 | −870 | −1010 |
| 40 | −670 | −930 | −1000 | −1010 |
| 60 | −680 | −950 | −1010 | −1020 |
| 80 | −800 | −960 | −1015 | — |
| 100 | −850 | −970 | −1020 | −1020 |
| 120 | −900 | −970 | −1020 | −1020 |
| 140 | −930 | −980 | — | — |
| 160 | −950 | −980 | — | — |
| 180 | −970 | −980 | −1020 | −1030 |
| 200 | −980 | −980 | — | — |

Figure 1:
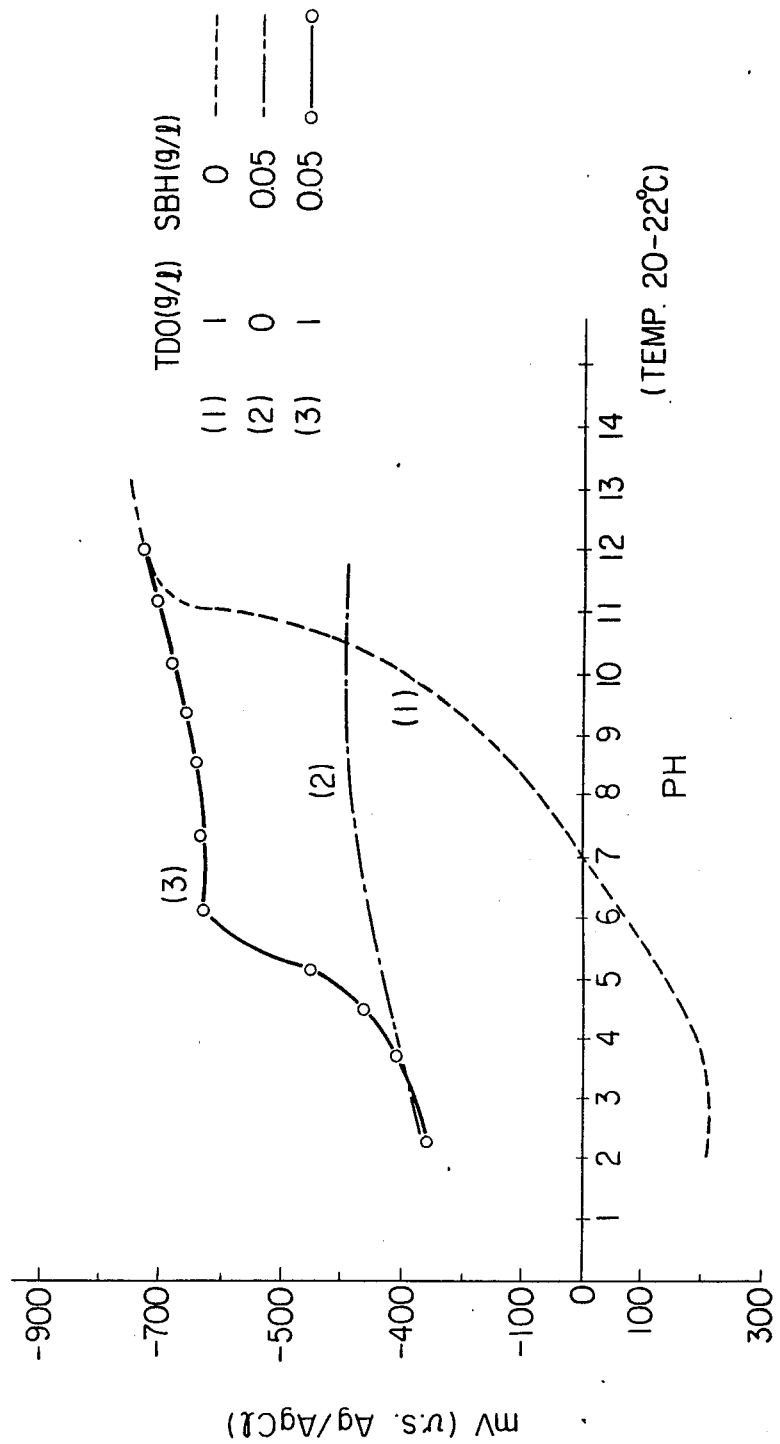
FIG. 1 is a diagram showing the relationship between pH and potential in Example 4.
Figure 2:
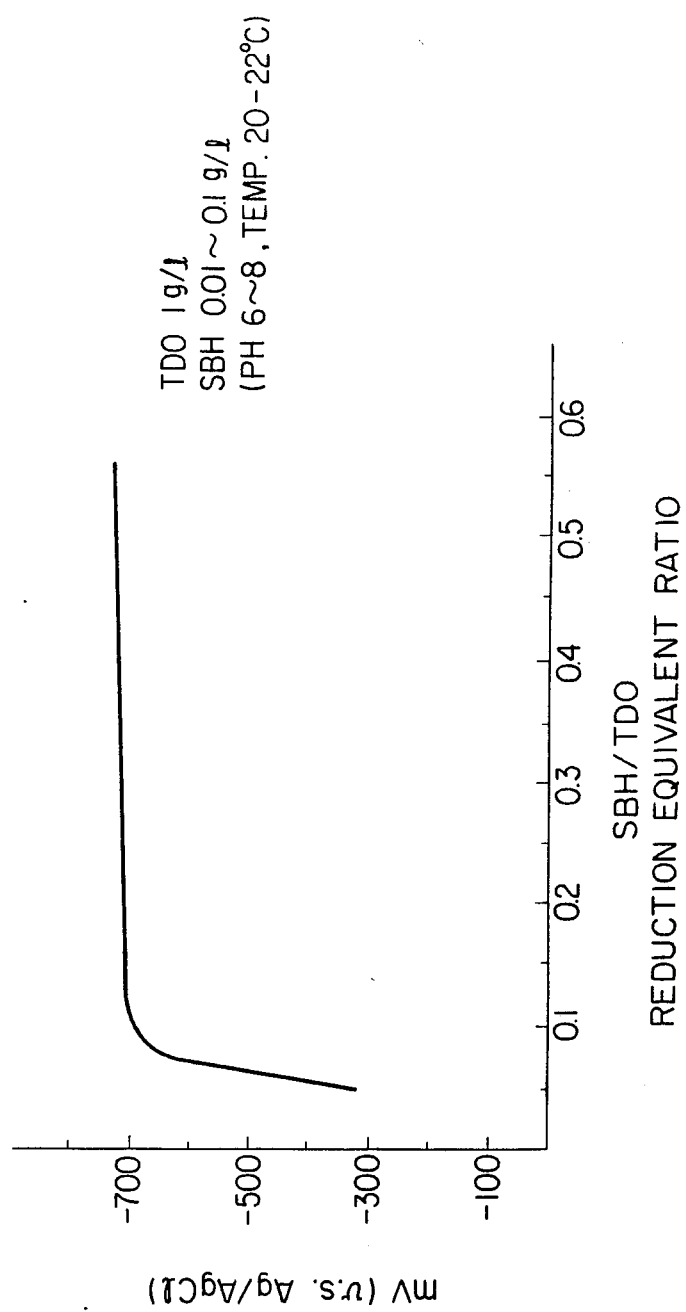
FIG. 2 is a diagram showing the relationship between SBH/TDO reduction equivalent ratio and potential in Example 5.
Figure 3:
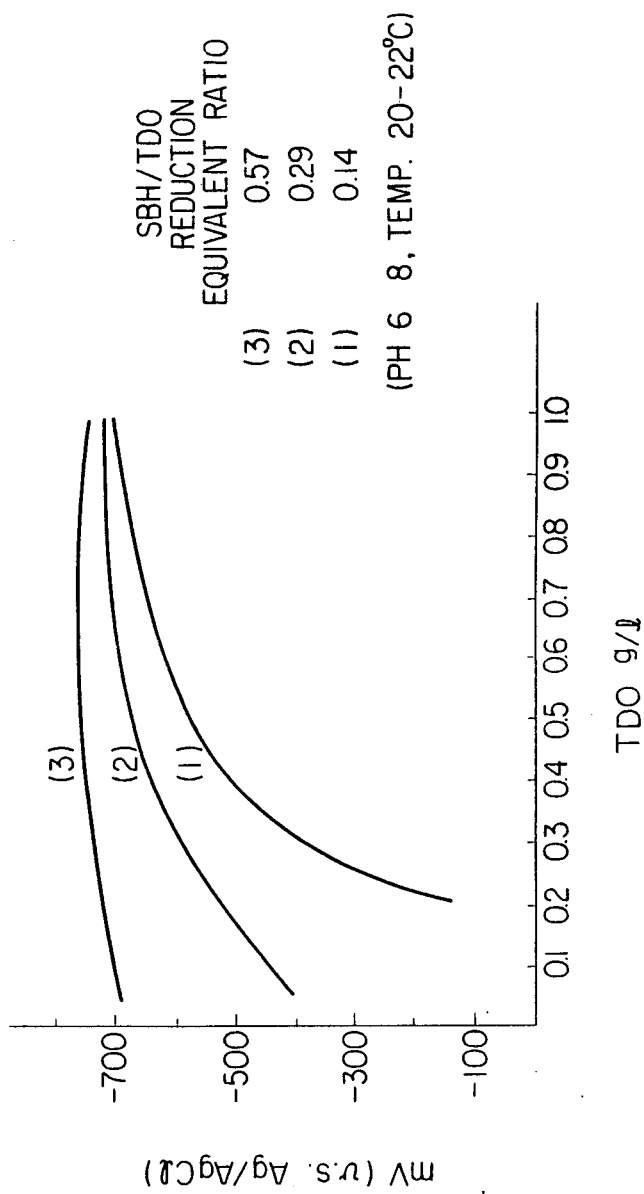
FIG. 3 is a diagram showing the relationship between TDO concentration and potential in Example 6.
Figure 4:
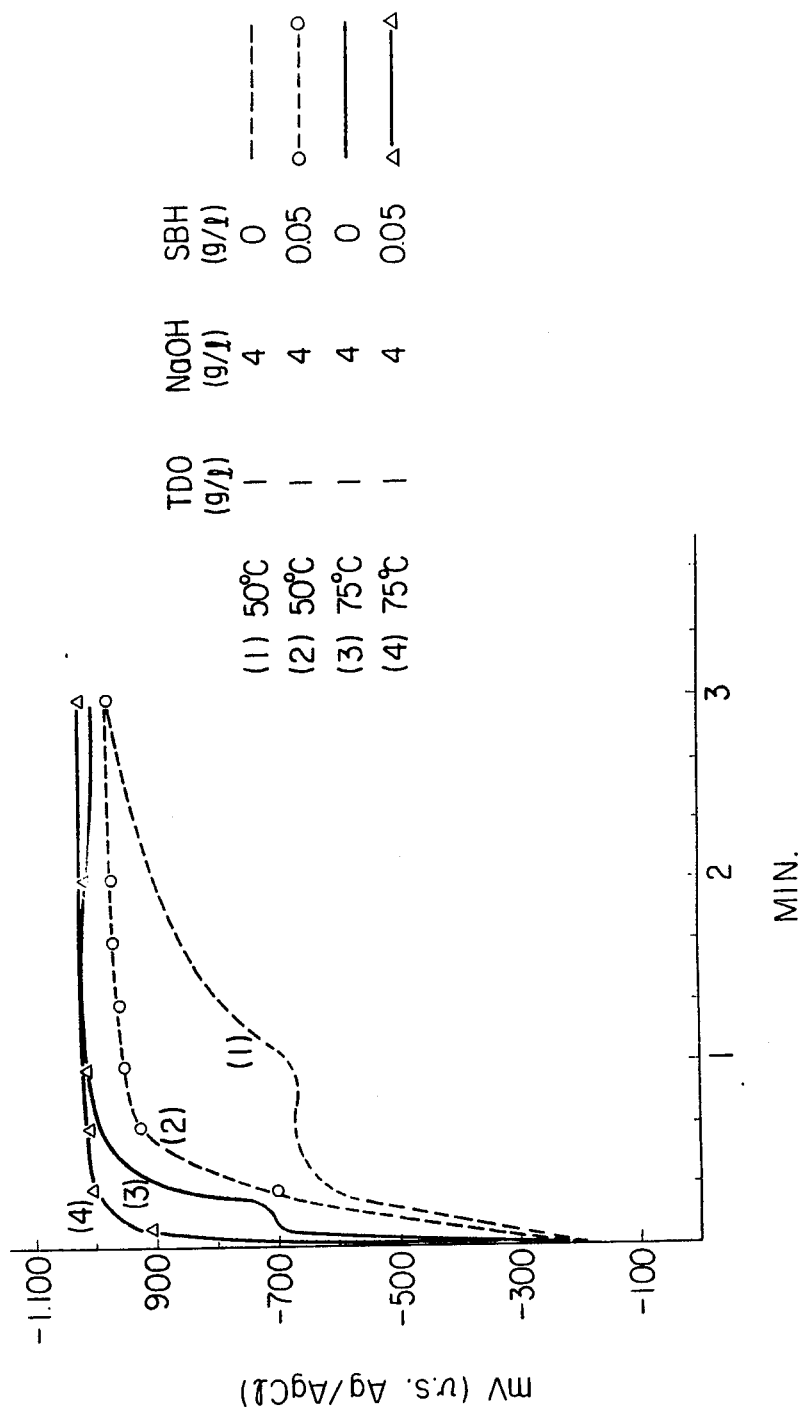
FIG. 4 is a diagram showing the relationship between time and potential in Examples 8 and 9.

What is claimed is:

1. A method of activating thiourea dioxide, characterized by incorporating in the thiourea dioxide a substance which dissolves in water or an acidic aqueous solution and produces hydrogen.

2. The method of claim 1, wherein said hydrogen-producing substance is a member selected from the group consisting of K, Na, Mg, Al, Zn, Sn, borohydride salts and lithium aluminum hydride.

3. The method of claim 1, wherein said hydrogen-producing substance is used in an amount not less than 0.01 in terms of a ratio of reduction equivalent of hydrogen produced therefrom to that of thiourea dioxide.

4. The method of claim 1, wherein the thiourea dioxide is in the form of an aqueous solution.

* * * * *